US010165960B2

(12) United States Patent
Forman et al.

(10) Patent No.: US 10,165,960 B2
(45) Date of Patent: Jan. 1, 2019

(54) MAGNETIC RESONANCE 2D NAVIGATOR TECHNIQUE

(71) Applicant: Siemens Healthcare GmbH, Erlangen (DE)

(72) Inventors: Christoph Forman, Erlangen (DE); Ivo Prochaska, Vaihingen an der Enz (DE); Jens Wetzl, Spardorf (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/935,371

(22) Filed: Mar. 26, 2018

(65) Prior Publication Data

US 2018/0271400 A1 Sep. 27, 2018

(30) Foreign Application Priority Data

Mar. 27, 2017 (EP) ..................................... 17162995

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/0044* (2013.01); *A61B 5/7207* (2013.01);
(Continued)

(58) Field of Classification Search
USPC ........................................................ 382/128
See application file for complete search history.

(56) References Cited

U.S. PATENT DOCUMENTS

| 7,348,776 | B1 * | 3/2008 | Aksoy | G01R 33/5611 |
| | | | | 324/307 |
| 7,945,305 | B2 * | 5/2011 | Aggarwal | G01R 33/5673 |
| | | | | 600/407 |
| 8,086,003 | B2 * | 12/2011 | Pfeuffer | G01R 33/56509 |
| | | | | 324/307 |
| 8,183,864 | B2 * | 5/2012 | Xu | A61B 5/055 |
| | | | | 324/307 |

(Continued)

OTHER PUBLICATIONS

Wetzl, et al.: "Free-Breathing, Self-Navigated Isotropic 3-D CINE Imaging of the Whole Heart Using Cartesian Sampling";: Proc. Intl. Soc. Mag. Reson. Med.; vol. 24; 2016; abstract No. 411.(2016).

(Continued)

*Primary Examiner* — Ishrat I Sherali
(74) *Attorney, Agent, or Firm* — Schiff Hardin LLP

(57) ABSTRACT

In a method and apparatus for producing respiration-corrected MR images of an examination volume containing the heart of a patient during respiratory movement of MR signals are recorded continuously during multiple cardiac cycles, each cardiac cycle having multiple time segments. One 2D navigator image data record per cardiac cycle is recorded during a time segment of that cardiac cycle, with k-space being filled along a Cartesian trajectory such that a spatial resolution is achieved in two spatial directions of the examination volume. Also, multiple 3D image data records are recorded in the other time segments of that cardiac cycle, with Cartesian filling of raw data space such that a spatial resolution is achieved in all three spatial directions of the examination volume. The respiratory movement is then determined from these navigator data records. The determined respiratory movement is corrected in the recorded MR signals.

11 Claims, 3 Drawing Sheets

(51) Int. Cl.
*G06T 11/00* (2006.01)
*G01R 33/48* (2006.01)
*G01R 33/561* (2006.01)
*G01R 33/565* (2006.01)

(52) U.S. Cl.
CPC ..... *G01R 33/4822* (2013.01); *G01R 33/5614* (2013.01); *G01R 33/56509* (2013.01); *G06T 11/005* (2013.01); *G06T 11/008* (2013.01); *A61B 2576/023* (2013.01); *G06T 2210/41* (2013.01)

(56) References Cited

U.S. PATENT DOCUMENTS

| | | | | |
|---|---|---|---|---|
| 8,427,153 | B2* | 4/2013 | Hu | G01R 33/3415 |
| | | | | 324/309 |
| 9,271,661 | B2* | 3/2016 | Moghari | A61B 5/7207 |
| 2016/0252596 | A1* | 9/2016 | Nielsen | G01R 33/482 |
| | | | | 324/309 |
| 2017/0076449 | A1* | 3/2017 | Chow | G06T 7/0012 |

OTHER PUBLICATIONS

Keigo et al: "Direct Coronary Artery Motion Tracking from Cartesian 2D Fat Image Navigator for Motion Corrected Coronary MRA", Proceedings of the International Society for Magnetic Resonance in Medicine, ISMRM, 20th Annual Meeting and Exhibition, Melbourne, Australia, May 5-11, 2012, Apr. 21, 2012 p. 3813,; (2012).

Henningsson et al: "Whole-heart coronary MR angiography Using Image-Based Navigation for the Detection of Coronary Anomalies in Adult Patients With Congenital Heart Disease : Image-Navigated Coronary MRA". Journal of Magnetic Resonance Imaging, vol. 43, No. 4, pp. 947-955, (2015).

Prochaska et al: "Feasibility Study: 2-D Self-Navigation using Compressed Sensing Reconstruction for Respiratory Gating in Free-breathing 3-D CINE Imaging", International Society for Magnetic Resonance in Medicine, ISMRM, 2030 No. 3161, p. 3161, (2017).

Piccini et al.: "Respiratory Self-Navigation for Whole-Heart Bright-Blood Coronary MRI: Methods for Robust Isolation and Automatic Segmentation of the Blood Pool", Magnetic Resonance in Medicine, vol. 68, pp. 571-579, (2012).

Coppo, et al.: "Free-Running 4D Whole-Heart Self-Navigated Golden Angle MRI: Initial Results"; Magnetic Resonance in Medicine; vol. 74; pp. 1306-1316; (2015).

Henningsson, et al.. Prospective Respiratory Motion Correction for Coronary MR Angiography Using a 2D Image Navigator. Magnetic Resonance in Medicine, vol. 69, pp. 486-494.; (2013).

Lustig et al., Compressed Sensing MRI, IEEE Signal Processing Magazine (72), pp. 72-82; (2008).

* cited by examiner

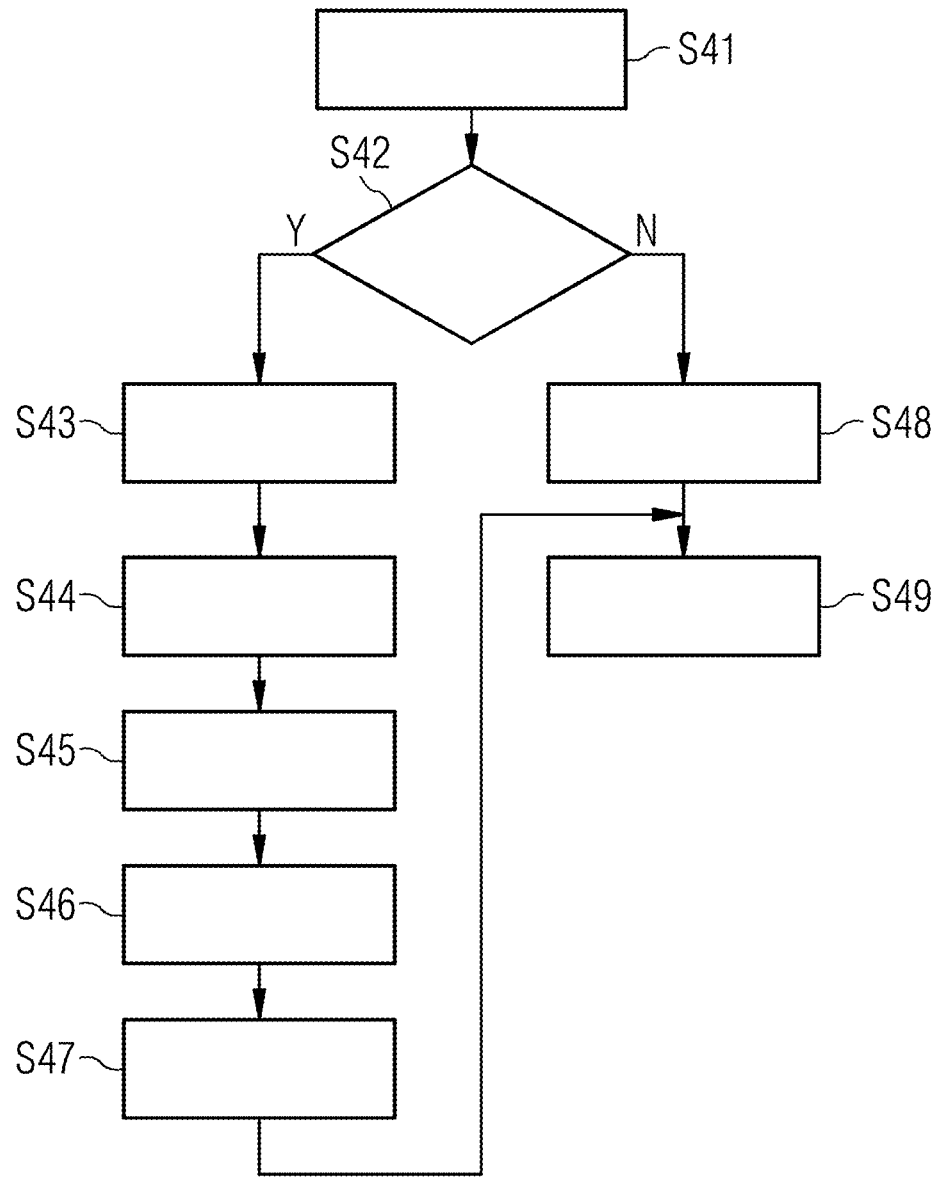

MAGNETIC RESONANCE 2D NAVIGATOR TECHNIQUE

BACKGROUND OF THE INVENTION

Field of the Invention

The present invention concerns a method for producing respiration-corrected magnetic resonance (MR) images of an examination volume of a patient while respiratory movement of the patient occurs, wherein the examination volume contains the heart. The invention further relates to an MR apparatus and a non-transitory, electronically readable data storage medium that implements such a method.

Description of the Prior Art

When producing 3D images of the heart relative to time, so-called CINE images, the total acquisition time is typically between three and five minutes. These recordings cannot be made using the breath-holding technique, and therefore the patient breathes freely during the recording of the MR data. This respiration-induced movement results in artifacts in the reconstructed MR images. For the purpose of three-dimensional imaging of the heart in a cardiac phase, e.g. coronary angiography (MRA), there are various methods for detecting and compensating the respiratory movement during the examinations. Using the navigator technique, the respiratory movement is detected and can then be taken into consideration when calculating the MR images in order to compensate the respiratory movement. External navigators are usually employed, so an external device, such as a respiratory belt or other devices, detects the respiratory movement, and the respiratory movement is then taken into consideration either during the image recording or during the image reconstruction. Also known are image-navigator or auto-navigator techniques, wherein the MR images themselves are used to deduce the respiratory movement on the basis of the recorded MR signals.

For the purpose of dynamic 3D imaging of the heart, the MR signals must be recorded continuously over the cardiac cycle in order to obtain images for the various time points of the cardiac cycle. In the context of this continuous data recording over the cardiac cycle, the auto-navigator technique is the technique of choice since this is the only option for detecting the respiration if delay times for the acquisition of specific navigator data are to be avoided. For the three-dimensional representation of the heart, usually so-called 1D auto-navigator techniques are used, in which a line in the center of the raw data space (k-space) is periodically recorded in a superior-inferior direction, i.e. from the head toward the feet. Each point in the Fourier transformation of this line represents a projection of an axial plane of the upper part of the body. In the case of measurements involving multiple reception coils, the respiratory movement can also be detected using an image from a single coil instead of combining the data from all coils. This single coil must be selected manually by checking image data that have been recorded, and therefore the reconstruction is not completely automatic in this case. This one-dimensional information can then be used to calculate a respiratory curve so that this can be taken into consideration when recording the actual MR image data, whether this is achieved by so-called gating functions, in which only data from a specific respiratory phase is taken into consideration, or by other techniques in which the respiration-induced movement is corrected in the MR images.

SUMMARY OF THE INVENTION

An object of the invention is to further improve and to automate the respiratory correction, in particular to improve the detection and quantification of the respiratory movement.

According to a first aspect of the invention, a method is provided for producing respiration-corrected MR images of an examination volume of a patient, wherein the patient is breathing and the examination volume includes the heart. Recordings of MR signals of the examination volume are generated continuously during a number of cardiac cycles, each cardiac cycle including a number of time segments. The continuous recording is implemented by computer controlled operation of an MR apparatus. As part of this continuous recording, at least one 2D navigator image data record per cardiac cycle is recorded during a time segment of that cardiac cycle, by which the examination volume is excited and raw data space (k-space) is filled with MR signals by making data entries along a Cartesian trajectory such that a spatial resolution is achieved in two of three spatial directions of the examination volume. A number of 3D image data records are also recorded during the other time segments of the cardiac cycle, wherein each of these image data records is raw data space filled with MR signals entered along a Cartesian trajectory such that a spatial resolution is achieved in all three spatial directions of the examination volume. The determination of the respiratory movement then takes place in the same computer that controlled the continuous recording, or in a different computer, using the navigator image data records that were recorded over the various cardiac cycles. MR images are reconstructed from the MR signals recording in the cardiac cycles. Respiration-corrected MR images are generated by correcting effects of the determined respiratory movement, represented in the recorded MR signals, on the reconstructed images. The correction of the respiratory movement can take place before reconstruction by "gating", in which only image data records from a specific respiratory phase are used for the reconstruction, or the respiratory movement is corrected in the reconstructed MR images by removing the effect therein of the respiratory movement represented in the MR signals. The reception-corrected MR images are made available from the computer in electronic form, as at least one data file.

By virtue of the spatial resolution in two of the three dimensions for the navigator image data record, it is possible to precisely detect various anatomical regions and the movement thereof. As a result of using Cartesian recording trajectories in which raw data space is filled with raw data in a Cartesian manner, it is possible to use fast and simpler image reconstruction methods. By virtue of the two-dimensional determination of the movement, it is also possible to use a movement compensation in two directions. Each point of a 2D navigation image can be a projection of a right-to-left line of the upper part of the body.

The cardiac cycle is divided into a number of cardiac phases and each cardiac phase preferably has a number of time segments. The 2D navigator image data records are all recorded during a defined cardiac phase, e.g. the diastole. The recording of the navigator image data records can however take place such that they are recorded in different time segments of this cardiac phase (the diastole). The recording of the navigator image data records does not always take place in the same time segment during a cardiac phase, but is distributed over a number of time segments in this cardiac phase. It is thereby possible to avoid the case of no three-dimensional image data records, which are required for the production of a film (movie) on the basis of the MR images, being recorded from a time segment.

For the purpose of recording the 2D navigation data records and the 3D image data records, a 3D BSSFP (Balanced Steady State Free Precession) imaging sequence can be used. Use of this sequence results in a steady state in the development of the magnetization; the MR signal does not completely relax back into the quiescent state. In the spatial resolution, the navigator image data records and the 3D image data records can differ only in the third dimension; the excitation volume is preferably identical. In the present case, such a sequence has the advantage that it is not necessary to wait for the complete relaxation of the excited nuclear spin before a recording of the navigator image data records can take place.

By virtue of the two-dimensional navigator image data records, the movement of a defined anatomical region or various anatomical regions can be used to determine the respiratory movement, e.g. the two-dimensional movement of the diaphragm, the chest or the liver. When recording the 2D navigator image data records, raw data space in one of the two directions in which a spatial resolution takes place is preferably not completely filled with raw data according to the Nyquist criterion. Likewise when recording the 3D image data records, raw data space in two of the three spatial directions in which a spatial resolution takes place is not completely filled with raw data according to the Nyquist criterion. The image reconstruction of the MR images of the navigator image data records and the image data records is preferably performed using Compressed Sensing Technology, which can be used in the case of undersampled data, particularly when a large proportion of the image points do not have a strong signal intensity after applying a mathematical transformation of the generated MR images, e.g. the wavelet transformation.

The navigator image data records and the image data records can be used to calculate the respiration-corrected MR images, which can be represented relative to time in the CINE images. This means that the navigator image data records can also be used for image reconstruction, and not only for the purpose of determining the movement.

The cardiac cycle preferably are divided into a specified number of time segments, and either a 2D navigator image data record or a 3D image data record is recorded in each of the time segments. As part of this activity, the navigator image data records over the various cardiac cycles are distributed into the time segments of the defined cardiac phases such that 3D image data records are also recorded for every time segment of the defined cardiac phase. This means that one navigator image data record is preferably recorded per cardiac cycle, and 3D image data records are recorded in all other time segments, but the navigator image data records are not always recorded in the same time segment relative to the cardiac cycle.

The invention also encompasses an associated MR apparatus, which has a control computer and a memory. The memory stores control information (code) that which can be executed by the control computer. The control information cause the control computer of the MR apparatus to be operated so as to execute the steps described above.

The present invention also encompasses a non-transitory, computer-readable data storage medium encoded with programming instructions that, when the storage medium is loaded into a computer or computer system of a magnetic resonance apparatus, cause the computer or computer system to operate the magnetic resonance apparatus so as to implement any or all embodiments of the method according to the invention, as described above.

The features described above and the features described below can be used not only in the corresponding combinations represented explicitly herein, but also in other combinations unless explicitly noted otherwise. It is also possible to use the various features individually.

BRIEF DESCRIPTION OF THE DRAWINGS

FIG. 4 is a flowchart of the steps that are performed when determining the respiration-corrected MR images of the heart in the MR apparatus of FIG. 1.

DESCRIPTION OF THE PREFERRED EMBODIMENTS

Figure 1:
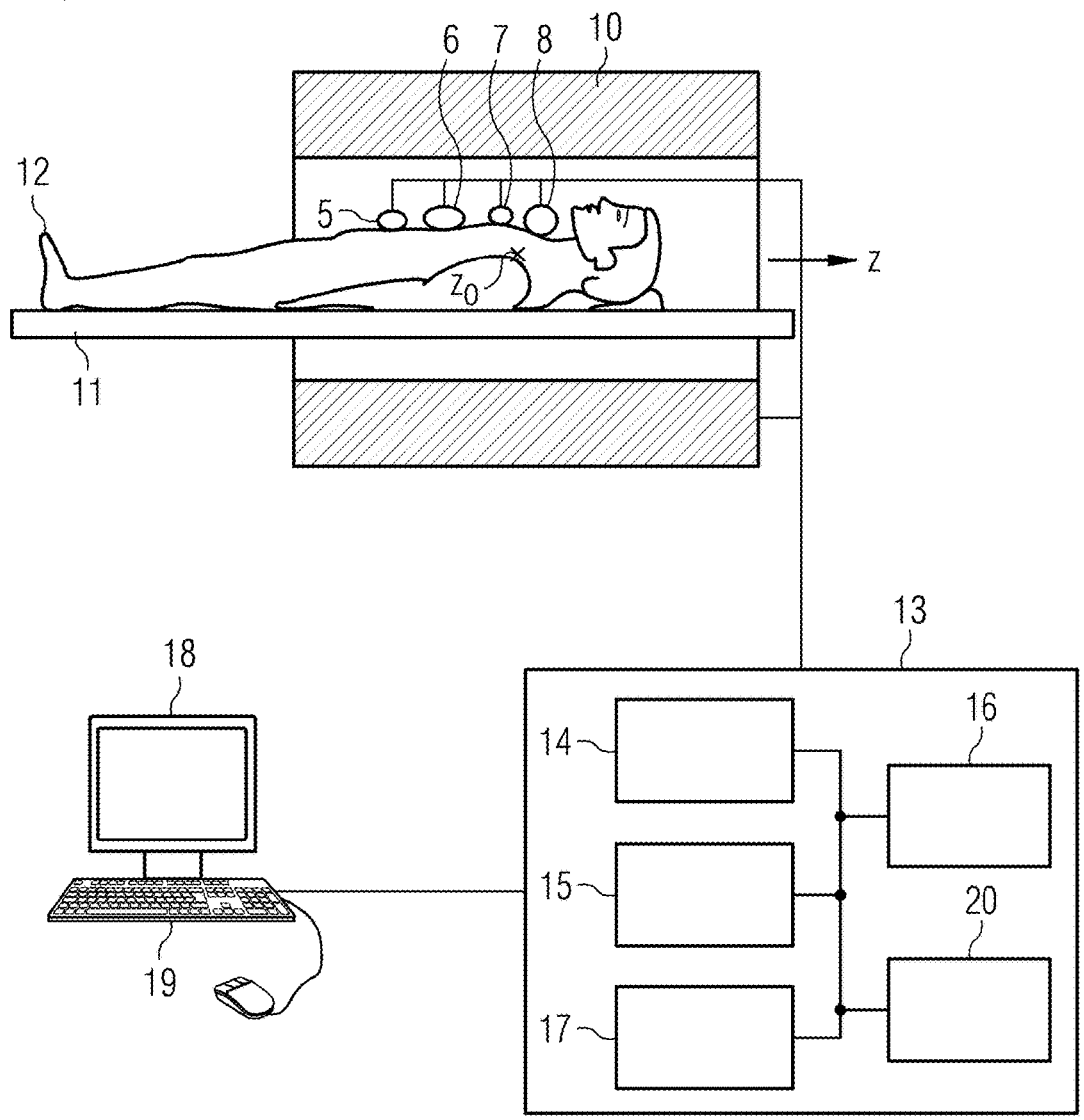
FIG. 1 schematically shows an MR apparatus with of which the respiration-corrected MR images of a heart can be recorded in accordance with the invention.

FIG. 1 schematically shows an MR apparatus with which respiration-corrected MR images of a patient can be recorded in accordance with the invention. The magnetic resonance apparatus has a scanner with a basic field magnet 10 that generates a polarization field B0, wherein a patient 12 on the bed 11 represents the examination object, which is moved into an isocenter Z0 of the magnet 10 in order to record magnetic resonance signals of the examination object, which are spatially encoded. By applying radio-frequency pulses and switching magnetic field gradients, the magnetization of certain nuclear produced by the polarization field BO can be disrupted by deflecting the nuclear spin from the position of equilibrium. The currents induced in receiving coils 5 to 8, as a result of the nuclear spins returning to the same original position, can be converted into magnetic resonance signals. The functions generally involved in the production of MR images with the detection of magnetic resonance signals are known to those skilled in the art, and therefore a more detailed description not necessary herein.

The examination installation has a control computer 13, which is used to control the MR installation. The control computer 13 has a gradient controller 14 and an RF controller 15 for switching and generating the RF pulses for deflecting the nuclear spins from the position of equilibrium. The RF unit can be a multichannel RF unit or a single-channel RF unit. A memory 16 stores imaging sequences that are required in order to record the MR images and any other control information that is required in order to execute the invention. An image sequence controller 17 controls the image recording and therefore, as a function of the selected imaging sequence, the sequence of the magnetic field gradients, the RF pulses and the reception intervals of the MR signals. The image sequence controller 17 therefore also controls the gradient controller 14 and the RF controller 15. MR images can be calculated in the computer 20 and displayed on a display monitor 18. An operator can control the MR installation via an input unit 19. In particular, the computer 20 and the image sequence controller 17 are designed so that the 2D navigator image data records are generated, wherein the computer 20 then identifies and quantifies the respiratory movement and calculates respiration-corrected MR images. The computer 20 can have one or more processors that process the control information that is stored in the memory 16.

The connections shown in FIG. 1 between the individual functional units can be hard-wired or wireless.

Figure 2:
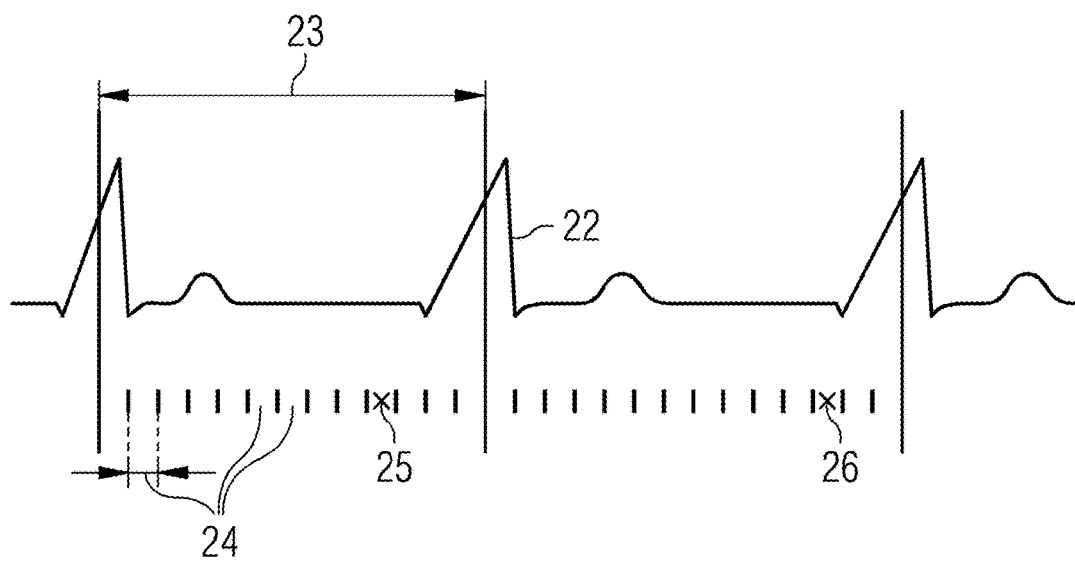
FIG. 2 schematically shows the division of the cardiac cycle into a number of time segments and the division of the cardiac cycle for the recording of image data records and navigator image data records.

Illustrated schematically in FIG. 2 is a temporal profile 22 of the cardiac activity. A cardiac cycle 23 is divided into a number of time segments 24. As explained in greater detail below, either a 3D image data record or a 2D navigator image data record is recorded during each of these time segments. The time segments in which a navigator image data record is recorded are shown by a cross, these being the time segments 25 and 26 in FIG. 2. It can be seen from the comparison between the first cardiac cycle and the second cardiac cycle that the recording of the navigator image data record does not take place in the same time segment in the temporal profile, but in different time segments of a cardiac phase, the diastole here. The recording preferably takes place such that a continuous recording of the MR signals takes place. If the cardiac cycle is divided into 20 time segments, for example, the 3D image data records are recorded in 19 time segments and the navigator image data records are recorded in one time segment. The 3D image data records are recorded in all time segments except for the time segments 25 and 26.

The 2D image data records are recorded using a BSSFP sequence, e.g. during the end of the diastolic phase of the cardiac cycle. An MR image is produced as a result of this two-dimensional Cartesian recording of the raw data space, wherein only the resolution in the third dimension of the excitation volume is illustrated in a cumulative manner. The two spatial directions in which a spatial resolution takes place can be the anterior-posterior direction and the superior-inferior direction, and therefore only averaging of the MR signals is available over the third dimension, the lateral direction. It is therefore possible, for example, to establish the position of the thorax and its movement in two dimensions, this being impossible in the case of one-dimensional navigator data. Of course, other organs or anatomical regions such as the liver or the diaphragm and their two-dimensional movement can also be used to determine the respiratory movement.

Figure 3:
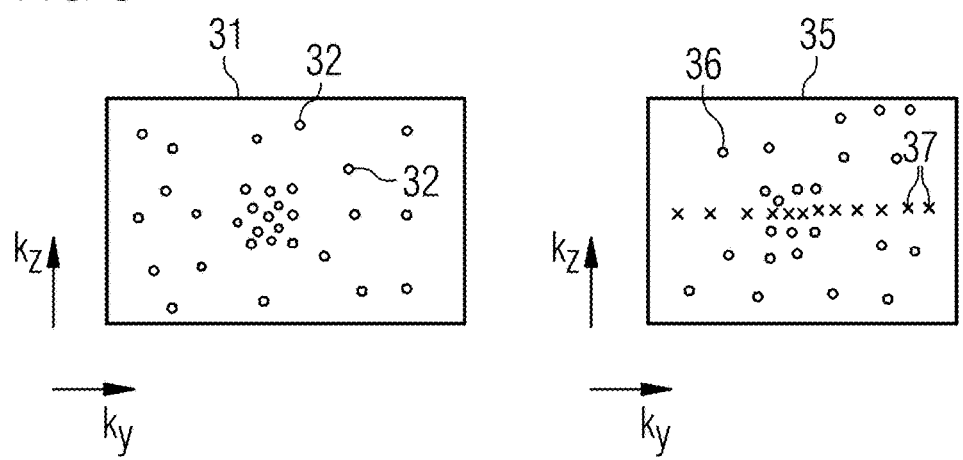
FIG. 3 schematically shows a recording model for two different cardiac phases of the cardiac cycle in the raw data space, wherein only image data records are recorded in the first cardiac phase and both image data records and navigator image data records are recorded in the other cardiac phase.

Illustrated schematically in FIG. 3 is raw data space for two different cardiac phases, and the manner in which raw data space is filled with raw data. The left side shows raw data space 31, which represents raw data space during the systolic cardiac phase. Each raw data point 32 corresponds to a recorded raw data line which extends into the plane of the drawing, i.e. the Kx direction here. The data recording in this context takes place such that the raw data points generate the 3D image data record, wherein undersampling occurs in the illustrated spatial directions Kz and Ky, such that the Nyquist criterion for an artifact-free reconstruction is not satisfied in these two directions Kz, Ky. The reconstruction of the 3D image data records can be performed using Compressed Sensing Technology. Raw data space 35 during a diastolic phase is represented on the right side of FIG. 3. Here again, the image data records are indicated by the raw data points 36, while the raw data points 37 indicate the raw data points at which the navigator image data records are recorded. It can be seen from the right image in FIG. 3 that the acquisitions for the navigator image data record are distributed over the various time segments of the diastolic cardiac phase, and therefore different image data records are available when Kz is not equal to zero. As shown by the raw data record 35 in FIG. 3, all navigator image data recordings take place when Kz is equal to zero, and therefore no spatial resolution is available in this third spatial direction. This 2D projection data record is likewise undersampled in one of the spatial directions, Ky in this case, and can be recorded using the TPAT (Temporal Parallel Acquisition Technique), for example.

The data reconstruction can then be performed in two steps using the Compressed Sensing Technology. In a first step, the navigator image data records are filtered out of the continuous data recording, i.e. they are determined. These data records are then reconstructed and used to determine the movement.

The method for producing the respiration-corrected MR images is explained again with reference to FIG. 4. In step S 41, a continuous signal recording takes place. In step S 42, a check then establishes whether this is the first pass in the method. If so, in step S 43 the navigator image data records are determined in the continuous signal recording. As explained with reference to FIGS. 2 and 3, the navigator image data records differ from the image data records in that they are only spatially resolved in two spatial directions instead of the three spatial directions for the image data records. The reconstruction of the navigator image data records then takes place in the step S 44. In step S 45, the anatomical region or regions are identified which will be used to determine the respiratory movement. The movement detection can be determined in various ways. For example, the heart can be specified as the region of interest and all of the images can then be registered to form a reference navigator image data record. Using the movement fields that were determined by the registration, it is possible to calculate the mean value for the size of the movement and if the movement is less than a defined limit value, the data from this time segment can be used for the reconstruction of the respiration-corrected MR images.

The respiratory movement can also be determined by searching for structural similarities in the navigator image data records. Using this method known as Structural Similarity (SSIM), the complete MR images or parts thereof are compared with each other and the data is used if the similarity value is greater than a defined limit value. A further possibility consists in segmenting the heart in all navigator image data records. The core of the heart is then chosen as a reference location and all recordings of the 3D image data records are used in which the core lies at the same location.

After determining the respiratory movement thus in step S 46, the 2D navigator image data records and the 3D image data records are filtered according to the respiratory phase in step S 47 if only images of an individual respiratory phase are to be taken into consideration (step S 47). This filtering according to the respiratory phase is not essential, however, and images of all respiratory phases can also be taken into consideration.

If it was established in step S 42 that the respiratory movement was determined in the first pass, the MR data records can again be filtered according to the respiratory phase in step S 48, in order to take only a specific respiratory phase into consideration, before the respiration-corrected MR signals are produced in step S 49.

The method described above has the advantage that the whole upper part of the body including lungs, liver and heart can be represented in the navigator image data record, and therefore the position of the heart can be monitored effectively. It allows movement compensation in two directions. A further advantage is that the method described above can be completely automated. Interaction with an operator of the MR installation is not necessarily required.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for producing respiration-corrected magnetic resonance (MR) images of an examination volume, containing the heart, of a patient exhibiting respiratory movement, said method comprising:
   with a computer, operating an MR apparatus so as to execute a computer-controlled continuous recording of MR signals from the examination volume during a plurality of cardiac cycles of the heart, wherein each cardiac cycle comprises a plurality of time segments;
   with said computer, operating said MR apparatus so as to execute said computer-controlled continuous recording of MR signals by recording one 2D navigator data record in each cardiac cycle during a time segment of each respective cardiac cycle, by exciting nuclear spins in the examination volume so as to produce raw MR data and entering the raw MR data into k-space along a Cartesian trajectory in order to form each 2D navigator data record with a spatial resolution in two of three spatial directions of the examination volume, and by also recording a plurality of 3D image data records in each cardiac cycle during respective time segments of a respective cardiac cycle other than the time segment in which said 2D navigator data record was recorded, by acquiring further raw MR data and entering said further raw MR data into k-space along a Cartesian trajectory in order to form each of said plurality of 3D image data records with a spatial resolution in all three spatial directions of the examination volume;
   in said computer, determining said respiratory movement from said 2D navigator data records respectively recorded in said plurality of cardiac cycles;
   in said computer, reconstructing MR images of the examination volume from the respective 3D image data records respectively recorded in said plurality of cardiac cycles; and
   in said computer, using said determined respiratory movement, either before or after reconstruction of said MR images, in order to compensate effects of said respiratory movement in said MR images, thereby producing respiration-corrected MR images, and making the respiration-corrected MR images available from the computer in electronic form, as at least one data file.

2. A method as claimed in claim 1 wherein said cardiac cycle comprises multiple cardiac phases and each of said cardiac phases has a plurality of said time segments therein, and comprising operating said MR apparatus to execute said computer-controlled continuous recording of MR signals so as to record each of said 2D navigator records during a same cardiac phase but in respectively different time segments of said same cardiac phase.

3. A method as claimed in claim 2 comprising operating said MR apparatus in order to execute said computer-controlled continuous recording of MR signals with said same cardiac phase being the diastolic phase of the heart.

4. A method as claimed in claim 1 comprising operating said MR apparatus in order to execute said computer-controlled continuous recording of MR signals by executing a 3D Balanced Steady State Free Precession Sequence in order to record each 2D navigator data record and each 3D image data record.

5. A method as claimed in claim 1 comprising determining said respiratory movement by identifying a movement of at least one predetermined anatomical region, within the examination volume, that is represented in each 2D navigator data record.

6. A method as claimed in claim 1 wherein operating said MR apparatus in order to execute said computer-controlled continuous acquisition of MR signals comprises entering the acquired raw MR data into k-space of each 2D navigator data record in one of said two directions of said spatial resolution with incomplete filling according the Nyquist criterion, and entering the acquired further MR data into k-space of each of said 3D image data records in two of said three spatial directions of said spatial resolution with incomplete filling according to the Nyquist criterion, and determining said respiratory motion and reconstructing the MR images from each 3D image data record using a compressed sensing technique.

7. A method as claimed in claim 1 comprising producing said respiration-corrected MR images so as to represent a temporal profile of said heart movement that is calculated in said computer using said 2D navigator data records and said 3D image data records.

8. A method as claimed in claim 1 wherein said cardiac cycle comprises multiple cardiac phases and each of said cardiac phases has a plurality of said time segments therein, and comprising operating said MR apparatus to execute said computer-controlled continuous recording of MR signals so as to record each of said 2D navigator records during a same cardiac phase but in respectively different time segments of said same cardiac phase, and wherein MR signals for either a 2D navigator data record or MR signals for a 3D image data record are recorded in each time segment of said same cardiac phase, with the 2D navigator data records being recorded in different time segments in said same cardiac phase from cardiac cycle-to-cardiac cycle, so that, in said plurality of cardiac cycles, a 3D image data record is recorded for every time segment of said same cardiac phase.

9. A method as claimed in claim 1 comprising determining and correcting for said respiratory movement in each of said two spatial directions of said 2D navigator data records.

10. A magnetic resonance (MR) apparatus for producing respiration-corrected MR images of an examination volume, containing the heart, of a patient exhibiting respiratory movement, said MR apparatus comprising:
    an MR data acquisition scanner;
    a computer configured to operate said MR data acquisition scanner so as to execute a computer-controlled continuous recording of MR signals from the examination volume during a plurality of cardiac cycles of the heart, wherein each cardiac cycle comprises a plurality of time segments;
    said computer being configured to operate said MR apparatus so as to execute said computer-controlled continuous recording of MR signals in order to record one 2D navigator data record in each cardiac cycle during a time segment of each respective cardiac cycle, by exciting nuclear spins in the examination volume so as to produce raw MR data and entering the raw MR data into k-space along a Cartesian trajectory in order to form each 2D navigator data record with a spatial resolution in two of three spatial directions of the examination volume, and in order to also record a plurality of 3D image data records in each cardiac cycle during respective time segments of a respective cardiac cycle other than the time segment in which said 2D navigator data record was recorded, by acquiring further raw MR data and entering said further raw MR data into k-space along a Cartesian trajectory in order to form each of said plurality of 3D image data records with a spatial resolution in all three spatial directions of the examination volume;

in said computer, determining said respiratory movement from said 2D navigator data records respectively recorded in said plurality of cardiac cycles;

said computer being configured to reconstruct MR images of the examination volume from the 3D image data records respectively recorded in said plurality of cardiac cycles; and said computer being configured to use said determined respiratory movement, either before or after reconstruction of said MR images, in order to compensate effects of said respiratory movement in said MR images, thereby producing respiration-corrected MR images, and making the respiration-corrected MR images available from the computer in electronic form, as at least one data file.

11. A non-transitory, computer-readable data storage medium encoded with programming instructions, said storage medium being loaded into a computer system of a magnetic resonance (MR) apparatus in order to produce respiration-corrected MR images of an examination volume, containing the heart, of a patient exhibiting respiratory movement, said programming instructions causing said computer system to:

operating the MR apparatus so as to execute a computer-controlled continuous recording of MR signals from the examination volume during a plurality of cardiac cycles of the heart, wherein each cardiac cycle comprises a plurality of time segments;

operate said MR apparatus so as to execute said computer-controlled continuous recording of MR signals by recording one 2D navigator data record in each cardiac cycle during a time segment of each respective cardiac cycle, by exciting nuclear spins in the examination volume so as to produce raw MR data and entering the raw MR data into k-space along a Cartesian trajectory in order to form each 2D navigator data record with a spatial resolution in two of three spatial directions of the examination volume, and by also recording a plurality of 3D image data records in each cardiac cycle during respective time segments of a respective cardiac cycle other than the time segment in which said 2D navigator data record was recorded, by acquiring further raw MR data and entering said further raw MR data into k-space along a Cartesian trajectory in order to form each of said plurality of 3D image data records with a spatial resolution in all three spatial directions of the examination volume;

determine said respiratory movement from said 2D navigator data records respectively recorded in said plurality of cardiac cycles;

reconstruct MR images of the examination volume from the 3D image data records respectively recorded in said plurality of cardiac cycles; and use said determined respiratory movement, either before or after reconstruction of said MR images, in order to compensate effects of said respiratory movement in said MR images, thereby producing respiration-corrected MR images, and make the respiration-corrected MR images available from the computer in electronic form, as at least one data file.

* * * * *